US006476217B1

(12) United States Patent
Tamion

(10) Patent No.: US 6,476,217 B1
(45) Date of Patent: Nov. 5, 2002

(54) METHOD OF PREPARING AN ALDOSE OR AN ALDOSE DERIVATIVE BY DECARBOXYLATION

(75) Inventor: Rodolphe Tamion, Allouagne (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 09/453,268

(22) Filed: Feb. 29, 2000

(30) Foreign Application Priority Data

Dec. 4, 1998 (FR) .............................. 98 15342

(51) Int. Cl.$^7$ ................................. C07H 1/00
(52) U.S. Cl. ..................................... 536/124
(58) Field of Search ................. 536/4.1, 124, 119, 536/121; 435/128

(56) References Cited

U.S. PATENT DOCUMENTS

| | | | |
|---|---|---|---|
| 3,755,294 A | | 8/1973 | Walon |
| 4,156,076 A | | 5/1979 | Dahlgren |
| 4,845,208 A | | 7/1989 | Fuertes et al. |
| 5,714,602 A | * | 2/1998 | Beck et al. ................. 536/124 |
| 5,739,303 A | * | 4/1998 | Beck et al. ................. 536/18.5 |
| 5,846,794 A | * | 12/1998 | Delobeau et al. ............ 435/158 |

FOREIGN PATENT DOCUMENTS

EP 716 067 6/1995

OTHER PUBLICATIONS

Albert L. Lehninger, "Biochemistry 2nd Ed.", Worth Publishers, Inc., (1975), pp. 249–251.*
O. Bortolini et al, "Metal Catalysis in Oxidation by Peroxides. Moybdenum– and Tungsten–Catalyzed Oxidations of Alcohols by Diluted Hydrogen Peroxide under Phase–Transfer Conditions", J. Org. Chem., 1986, vol. 51, pp. 2661–2663.*
Ron van den Berg et al, "Selective alkaline Oxidative Degradation of Mono– and DI–saccharides by H2O2 with Borate as Catalyst and Protecting Group", J. Chem. Soc. Perkin Trans. 1, 1994, pp. 1117–1118.*
Ruff O. Ber., 1889, vol. 32, p. 3672–3675.
Ruff O. Ber., 1900, vol. 30, p. 1798–1802.
Hockett R.C., J.A.C.S., 1934, vol. 56, p. 1632–1633.
J.A.C.S., 1950, vol. 72, p. 4546, Fletcher, H.G et al.
Dialog abstract in English in lieu of CZ 279 002, C A Abstract 123:33577.
Abstract in English in lieu of CZ 232 647.
Jacobson S.E., J. Org. Chem, 1979, vol. 44, p. 921–924.
Floor M., Starch/Stärke, 1989, vol. 41, pp. 303–309.
Sato K., Bull Chem. Soc. Jpn, 1997, vol. 70, p. 905–915.
Patent abstracts of Japan (JP 57 054198).

* cited by examiner

*Primary Examiner*—Sreeni Padmanabhan
*Assistant Examiner*—Paul A. Zucker
(74) *Attorney, Agent, or Firm*—Henderson & Sturm LLP

(57) ABSTRACT

The subject matter of the present invention is a method of manufacturing an aldose or an aldose derivative containing n carbon atoms on the hydrocarbonic chain, characterized by the fact that, in an aqueous phase, at least one acid derivative of saccharide with n+1 carbon atoms containing at least one α-hydroxy acid unit, and/or at least one salt of such an acid derivative of saccharide, is brought into contact with hydrogen peroxide in the presence of a quantity of at least one tungsten or molybdenum salt, said quantity being less than 4 equivalents, preferably less than 2 equivalents, expressed as the total number of moles of tungsten and molybdenum divided by the total number of moles of acid derivative(s) of saccharide and of salt(s) of acid derivative(s) of saccharide.

22 Claims, No Drawings

US 6,476,217 B1

METHOD OF PREPARING AN ALDOSE OR AN ALDOSE DERIVATIVE BY DECARBOXYLATION

BACKGROUND OF THE INVENTION

1. Field of the Invention

The subject matter of the present invention is a method of manufacturing an aldose or an aldose derivative.

More precisely, its subject matter is a method of manufacturing an aldose or an aldose derivative containing n carbon atoms on the hydrocarbonic chain, from an acid derivative of saccharide with n+1 carbon atoms having at least one α-hydroxy acid unit, and/or one of its salts, this method consisting in bringing said acid derivative of saccharide into contact with hydrogen peroxide (hydrogen peroxide) in the presence of at least one metal salt chosen from the group consisting of tungsten and molybdenum, in an aqueous phase.

In the sense of the present invention, the terms are agreed to mean the following:

"aldose": saccharide containing one aldehyde function, in particular a tetrose or a pentose containing such a function, preferably chosen from erythrose, threose, ribose, xylose and arabinose;

"aldose derivative": more particularly a uronic acid (monocarboxylic acid derived from an aldose by replacing the $CH_2OH$ group with a COOH group);

"acid derivative of saccharide containing at least one α-hydroxy acid unit": a mono- or dicarboxylic acid derived from an aldose, containing one CHOH function in α of the acid function or functions and being in free and/or lactonised form.

The method of the present invention makes it possible to obtain, with excellent selectivity, an aldose from an aldonic acid, or a uronic acid from an aldaric acid, in free or lactonised form, and/or in the form of salt(s).

The aldoses obtained by carrying out the method according to the invention are of great interest in themselves but would particularly be very important intermediate chemicals in synthesis if it were to come about that they could be produced in great quantity and at a low cost. In fact, a complementary stage of hydrogenation of these aldoses makes it possible easily to obtain the corresponding alditols which are all polyols able to be used in multiple applications, and particularly as substitutes for saccharose which are low-calorie and non-cariogenic.

The uronic acids obtained by carrying out the method according to the invention, as polyhydroxycarboxylic acids, have sequestering properties capable of being exploited in the field of cements, mortars or concretes in which such acids have been suggested as agents to retard setting, or even in the field of detergency where these acids have been proposed for cleaning articles made of glass or metal, or as additives for detergents.

2. Description of the Related Art

It is in studying the method explained by RUFF, almost a century ago (Ber. 32, 3674, (1889); 33, 1799 (1900)) that the Applicant has perfected this new method of manufacturing an aldose or an aldose derivative, by a chemical process, from an acid derivative of saccharide or from its salts.

RUFF's method makes it possible to pass, generally speaking, from an aldonic acid containing n carbons to an aldose containing (n−1) carbons thanks to the combined action of ferric ions and of hydrogen peroxide. However the yields of aldose are very mediocre.

The conversion of gluconic acid into D-arabinose can thus be realized according to this method.

Some improvements have subsequently been provided by R. C. Hockett and C. S. Hudson (J. Amer. Chem. Soc. 56, 1632–1633, (1934) and ibid. 72, 4546, (1950)) and by the inventors of U.S. Pat. No. 3,755,294. Yields of 60% of arabinose starting with gluconic acid are described there. Progress has also been made by V. Bilik (CZ—232647, (1983)), using cupric ions (Cu (II)) as catalysts. Yields of the order of 70% have been reached after laborious purification. Necessary in particular are the addition of ion exchange resins and column chromatography.

Identical results have been obtained recently with a mixture of ferric and ferrous ions as catalysts (CZ—279002, (1994)).

Finally, in particular conditions, document EP-A 0.716.067 reports yields of 78% of certain aldoses, but the technique also requires ion exchange chromatography in order to eliminate the impurities.

During an in-depth investigation of Ruff's reaction, the Applicant discovered that, if the reaction is catalyzed by selected concentrations of tungsten or molybdenum salts (both group VI metals), it is, unexpectedly, possible to resolve the problems of selectivity which accompanied prior methods and prevented their development.

Tungsten complexes are well cited as oxidation catalysts of secondary alcohols in ketones in the presence of hydrogen peroxide (S. E. Jacobson et al., J; Org. Chem, 44, 921–924, (1979)) or of starch and maltodextrins in oligomers having acid functions (M. Floor, Starch/Staërke, 41, 303–309, (1989)) or even as an epoxydizing agent of alkenes or an oxidation agent of primary and secondary alcohols in aldehydes and ketones (K. Sato, Bull. Chem. Soc. Jpn, 70, 905–915, (1997)).

The comparative performances of numerous salts, including sodium tungstate, as catalysts of the oxidation of carbohydrates, including glucono-delta-lactone ("GDL"). by hydrogen peroxide has been widely described by M. R. EVERETT and F. SHEPPARD in "Oxidation of Carbohydrates, Salt Catalysis", University of Oklahoma Medical School, 1944, pp. 25–90. However, the quantities of salts envisaged are very high, that is generally several "ion equivalents", i.e. several moles of the ion studied (anion or cation) per mole of carbohydrate.

Taking into account its poor efficiency, particularly with respect to bicarbonate anion which is presented as twice as efficient according to the second paragraph of page 44 of said document, the tungstate anion is used (in the form of sodium tungstate) at the rate of 4 equivalents with a view to catalyzing the oxidation, by hydrogen peroxide, of GDL provided in extremely diluted form (1% solution). The results presented in the tables VII page 42 and IX page 51 of said document do not, however, make it possible to know the exact nature and concentration of the product(s) resulting from the oxidation thus carried out in the presence of tungsten. In any case, the general teachings of this document go against the use of less than 4 equivalents of tungsten ions, taking into account the molecular mass of this metal (approximately 184) of less than 4×184, or approximately 736 g of tungsten, per mole of carbohydrate to be oxidized. Moreover, this document does not specifically envisage the use of molybdenum salts with a view to catalyzing the oxidation of carbohydrates by hydrogen peroxide.

Moreover, patent FR 2 346 451 envisages, in all generality and without giving examples, the possibility of using, amongst other catalysts, molybdenum oxides within the framework of the oxidation of gluconic acid into arabin saccharide. However, it is not unambiguously evident from the passage to be found on page 3, lines 17–26 of said patent, with which oxidant(s) the authors think it possible to associate the said molybdenum salts, and in particular whether it is a question of hydrogen peroxide, the use of which is exemplified in example 2 and/or of an acid such as peracetic acid (cf. example 8) or perbenzoic acid (cf. example 9). Whatever the case, the authors advocate quite particularly the combined use of hydrogen peroxide and of $Fe^{3+}$ ions and thus a standard RUFF method.

Thus none of the documents quoted above describes nor really suggests the interest of using a specific system of tungsten salt/hydrogen peroxide or molybdenum salt/hydrogen peroxide for the reaction of oxidative decarboxylation of an acid derivative of saccharide, or one of its salts, in an aqueous phase. In particular, nothing suggests that it is possible to increase the selectivity of said reaction considerably, which translates into the noteworthy reduction in the production of co-products such as formic acid.

This new catalyst thus has a significant potential and, to the knowledge of the Applicant Company, no equivalent reaction exists.

DETAILED DESCRIPTION OF THE INVENTION

In a surprising and unexpected manner, the Applicant has also noticed that it is possible to reduce the duration of the reaction significantly and also to increase significantly the selectivity of the reaction catalyzed by tungsten or molybdenum salts by associating with them doping agents, such as certain metallic types, in particular certain metallic salts, based on metals other than tungsten and molybdenum, particularly based on copper. In this connection, the Applicant found that copper salts like sulfates, acetates or copper chlorides, at a concentration of between 0.0001 and 1%, preferably between 0.001 and 0.5% were perfectly suitable. By way of example, 0.05% copper salt(s) is chosen. These values are understood in relation to the dry weight of the acid derivative(s) of the saccharide and of salt(s) of acid derivative(s) of the saccharide used. Such doping agents can be brought in by non de-mineralized water used instead of and in place of all or part of the aqueous component of the reaction medium.

Another advantage of the method according to the invention is that, by comparison with the methods of prior art, it is possible to use less hydrogen peroxide in the reaction medium.

Thus, according to the invention, the method of manufacturing an aldose or an aldose derivative containing n carbon atoms on the hydrocarbonic chain, is characterized by the fact that, in an aqueous phase, at least one acid derivative of saccharide with n+1 carbon atoms, containing at least one α-hydroxy acid unit, and/or at least one salt of such an acid derivative of saccharide are/is brought into contact with hydrogen peroxide in the presence of a quantity of at least one tungsten or molybdenum salt, less than 4 equivalents, preferably less than 2 equivalents, expressed as a total number of moles of tungsten and molybdenum divided by the total number of moles of acid derivative(s) of the saccharide and of salt(s) of acid derivative(s) of the saccharide.

The method according to the invention thus uses an acid derivative of saccharide and/or one of its salts. In the present invention, as indicated previously, what is meant by acid derivative of saccharide is a mono- or dicarboxylic acid derived from an aldose. This definition encompasses in particular:

- the aldonic acids, which are monocarboxylic acids derived from the aldoses by replacing the aldehyde group with a carboxy group such as gluconic, glucoheptonic, mannonic, idonic, gulonic, galactonic, lyxonic, xylonic, arabinonic, ribonic, maltobionic and lactobionic acids, and in particular gluconic acid, in free and/or lactonised form, the lactonised form being able advantageously to consist of glucono-δ-lactone (GDL),
- the aldaric acids, which are dicarboxylic acids derived from aldoses by replacing the two terminal groups (CHO and $CH_2OH$) with carboxy groups, such as glucaric, galactaric, arabinaric and xylaric acids,
- the uronic acids which are monocarboxylic acids derived from aldoses by replacing the terminal group $CH_2OH$ with a carboxy group, it being understood that these products are not the preferred acid derivatives of saccharide within the framework of the invention.

In the present invention, what is meant by "salt of an acid derivative of saccharide" is a product chosen from the group comprising the salts and esters of any acid derivative of saccharide such as defined above, and any mixtures of at least two of these products.

Thus, for example, alkaline and alkaline earth salts, in particular calcium and sodium salts of these acid derivatives of saccharide are perfectly suitable. These can be in particular calcium or sodium salts of gluconic acid.

The Applicant found that it was advantageous to use at least one acid derivative of saccharide, in free and/or lactonised form, within a mixture containing also at least one salt, preferably an alkaline or alkaline earth salt, of an acid derivative of saccharide.

As substrates capable of being brought into contact with hydrogen peroxide according to the invention, such mixtures have proved suitable for further improving the selectivity and yield of oxidation in respect of substrates consisting solely of acid derivatives of saccharide, in free and/or lactonised form.

These can be in particular, as exemplified below, mixtures containing GDL and at least one salt of gluconic acid, preferably sodium or calcium gluconate.

The dry weight of salt(s) of acid derivative of saccharide within such mixtures can especially represent between 0.5 and 20%, preferably between 1 and 10%, of the dry weight of acid derivative(s) of saccharide contained in such mixtures.

By way of example, this can be a mixture based on GDL and 2.5% approximately sodium gluconate, this percentage being expressed in dry weight of sodium gluconate over the dry weight of GDL.

According to another variant of the invention, the salt of acid derivative of saccharide, for example the salt of aldonic acid can be substituted, totally or partially, by a salt, especially alkaline or alkaline earth, of an acid other than an acid derivative of saccharide such as a salt of acetic acid, for example sodium acetate or a salt of an aromatic or aliphatic sulphonic acid, for example paratoluene sodium sulphonate.

The aldonic acids are obtained in known fashion by oxidation of the corresponding saccharide. This oxidation stage can be carried out either by a chemical process or by a microbiological process.

The preferred chemical process within the framework of the invention consists in oxidizing the saccharide with the aid of air or oxygen in an alkaline medium and with the aid of palladium catalysts.

A particularly preferred method is the one which has been described in the document U.S. Pat. No. 4,845,208, of which the Applicant is the proprietor, and which consists in using as an oxidation catalyst palladium fixed on activated charcoal and doped with bismuth.

It can be equally envisaged that the saccharide is oxidized by an electrolytic process or with the aid of hypobromite. In addition, it is possible to oxidize the saccharide by a microbiological process with the aid of Gluconobacter or Aspergillus.

The aldaric acids can be obtained, in known fashion, by oxidation of the corresponding saccharides in the presence of air and platinum.

Within the framework of the present invention, there is no particular constraint in terms of the dry matter of the reaction medium. In practice, the method according to the invention is characterized by the fact that any acid derivative of saccharide and/or any salt of acid derivative of saccharide is provided, in liquid and/or solid form, in a quantity such that the total concentration of acid derivative(s) of saccharide and of salt(s) of acid derivative(s) of saccharide, in the reaction medium, is between 1 and 90%, preferably between 20 and 90%, expressed in dry weight in relation to the total weight of the reaction medium. It is particularly noteworthy, as has been verified by the Applicant Company, that, contrary to what is usually recommended in standard RUFF reactions, it is possible to work here with high amounts of dry matter, for example with a value of between 30 and 60%, as is exemplified below.

Only the constraints of minimum amounts of dry matter are imposed for obvious reasons of saving water evaporation and reducing the size of the reactors, amounts of dry matter of 1% as used in the previously quoted EVERETT document not being economically viable in industrial practice.

In the following description, all the percentages are expressed in relation to the total acid derivative(s) of saccharide and salt(s) of acid derivative(s) of saccharide able to be present in the reaction medium, (example: 50 mol % signifies 50 moles of X for 100 moles, in total, of acid derivative(s) of saccharide and of salt(s) of such acid derivative(s), and 50% signifies 50 grams of X for 100 grams, in total, of acid derivative(s) of saccharide and of salt(s) of such acid derivative(s).

The tungsten and/or the molybdenum used as catalyst(s) of the reaction can be supplied, for example, in the form of oxides ($WO_3$ or $MoO_3$), acids ($H_2WO_4$ or $H_2MoO_4$), heteropolyacids of the KEGGIN or DAWSON type (phosphotungstic acid $H_3PW_{12}O_{40}$ or phosphomolybdic acid $H_3PMo_{12}O_{40}$, for example) or salts ($Na_2Wo_4$, $CaWo_4$ or $Na_2MoO_4$, $CaMoO_4$). However, the use is preferred of an alkaline, alkaline earth metal salt or an ammonium salt of tungsten or molybdenum such as, for example, sodium tungstate or molybdate, or ammonium molybdate.

According to a variant of the method according to the invention, the quantity of tungsten and/or molybdenum salt(s) in the presence of which the oxidation reaction occurs is less than 1 equivalent, expressed by the total number of moles of tungsten and molybdenum divided by the total number of moles of acid derivative(s) of saccharide with n+1 carbon atoms and of salt(s) of acid derivative(s) of saccharide.

By way of example, when the catalyst consists solely of tungsten salt(s) and the substrate consists solely of GDL, a quantity of tungsten salt(s) of 1 equivalent corresponds to 1 mole of tungsten per mole of GDL or, taking into account the respective molecular masses of tungsten (approximately 184) and of GDL (approximately 178), to a quantity of approximately 184/178 or roughly 1.03 or 103%, expressed in weight of tungsten in relation to the weight of GDL.

When the catalyst consists solely of molybdenum salt(s), the molecular mass of the molybdenum being 96 approximately, a quantity of molybdenum salt(s) of 1 equivalent corresponds, by the same type of calculation, to a quantity of roughly 0.54 or 54%, expressed in weight of molybdenum in relation to the weight of GDL.

A quantity of tungsten and/or molybdenum salt(s) of between 0.001 and 50%, preferably between 0.001 and 20% and more particularly between 0.001 and 10%, expressed in weight of tungsten and/or molybdenum in relation to the dry weight of acid derivative(s) of saccharide used and/or salt(s) of such acid derivative(s) of saccharide, gives good results in the method according to the invention as far as the yield and selectivity are concerned, as well as the purity of the aldose or aldose derivative. At least one doping agent can be added, as described above, such as copper sulfate or chloride and this at a total concentration of between 0.0001 and 1%, preferably between 0.001 and 0.5%, and for example 0.05%, this concentration being expressed in dry weight of doping agent(s) in relation to the total dry weight of acid derivative (s) of saccharide and of salt(s) of acid derivative(s) of saccharide able to be present in the reaction medium.

To the mixture of acid derivative(s) of saccharide and/or of associated salt(s), of catalyst and of water, there is slowly added, with stirring, hydrogen peroxide, preferably in the form of hydrogen peroxide of a strength of 25% to 70%, at a rate of 1 to 500 mol %, more particularly of 50 to 300 mol % in relation to the acid derivative of saccharide used, or to one of its salts.

The method according to the invention is implemented at a pH of between 1 and 8, depending on the form (acid, possibly lactonised, and/or salt(s)) of any acid derivative of saccharide introduced into the reaction medium.

By preference, the method of the invention is carried out at a temperature of between 0 and 100° C., preferably between 20 and 90° C., and especially between 20 and 50° C. approximately.

The hydrogen peroxide is added at an introduction speed such that the temperature of the reaction medium does not rise, preferably, beyond 60° C. Thus the introduction speed of the hydrogen peroxide is generally between 30 minutes and 20 hours, depending on the nature of the exothermic reaction.

Generally, temperatures lower than 20° C. lead to reaction times which are too long, and temperatures above 90° C., in addition to the fact that they would necessitate the use of reactors resistant to pressure, would lead to a degradation of the reaction products.

The invention will be better understood by means of the four examples which follow and which are intended solely to illustrate the invention better without in any way wishing to limit it to the forms of embodiment expressly described and to the acid derivative of saccharide used.

In the following examples, all the results are expressed in molar percentage.

EXAMPLE 1

Glucono-δ-lactone (91.9 grams, 0.516 mole), sodium tungstate dihydrate (0.5 grams, 1.5 mmoles) and water (500 ml) are introduced into a double envelope reactor. The mixture is raised to a temperature of 50° C. The hydrogen peroxide at 30% (110 ml, 1.1 moles) is introduced over 90 minutes without adjusting the pH of the reaction. When the addition has been completed, the solution is agitated until the peroxides have completely disappeared, or for 30 hours. The reaction mixture is then cooled down.

The conversion rate is 48% and the molar yield of D-arabinose is established as 30%.

The co-production of formic acid is only 18.5% (molar yield), whilst in standard conditions of the RUFF reaction, the latter is less selective and generates between 60 and 70% formic acid.

EXAMPLE 2

The reaction mixture is established in accordance with Example 1, but with the addition of 50 mg copper sulfate pentahydrate.

It is then noted that after 1.5 hours of reaction, the conversion rate reaches 93%, and the molar yield of D-arabinose is 80%. Moreover, no significant production of formic acid is deplored.

It emerges from the above that the use of such a doping agent is particularly favorable to the efficiency of the reaction, and this as much in terms of duration as of selectivity of the reaction.

The subject matter of the present invention is thus also a method such as described above, characterized by the fact that it is carried out in the presence of, at least, one doping agent chosen from metallic types, in particular metallic salts, based on metals other than tungsten and molybdenum, preferably chosen from copper salts.

EXAMPLE 3

Glucono-δ-lactone (184 g, 1.03 moles), sodium molybdate dihydrate (0.8 g, 0.0033 moles), copper sulfate pentahydrate (80 mg) and water (275 ml) are introduced into a double envelope reactor. The mixture is raised to 50° C. The hydrogen peroxide at 50% (77 ml, 1.34 moles) is introduced over 120 minutes. The reaction is slightly exothermic. When the addition has been completed, agitation is continued for 10 minutes and the mixture is then cooled down. The conversion rate is 84.6% and the yield of D-arabinose is 73.6%. Moreover, no significant production of formic acid is deplored either.

EXAMPLE 4

Glucono-δ-lactone (400 g, 2.24 moles) sodium gluconate (10 g, 0.046 mole) ammonium molybdate of the formula $(NH_4)_2 Mo_4O_{13}, 2H_2O$ (2.8 g including 1.62 g molybdenum or 0.017 mole molybdenum), copper sulfate pentahydrate (0.4 g) and water (1600 g) are introduced into a double envelope reactor. The mixture is raised to 30° C.

The hydrogen peroxide at 30% (600 ml, 5.9 moles) is added over 15 hours in total, this addition being interrupted, at the end of the sixteenth hour, by the addition of glucono-δ-lactone (400 g) and sodium gluconate (10 g) and by the homogenization of the reaction medium for 20 minutes. After this, the introduction of hydrogen peroxide is continued, for the remaining 9 hours, then the mixture is cooled down. The molar yield of D-arabinose is 91%.

This example shows that one can advantageously use, within the framework of the invention, a mixture containing an acid derivative of saccharide, in the case of glucono-δ-lactone (GDL), and a salt of an acid derivative of saccharide, in the case of sodium gluconate, as substrate for the oxidation reaction by means of hydrogen peroxide. In the present case, the quantity of salt of acid derivative of saccharide, i.e. 10 g+10 g=20 g (dry) represents 2.5% of the quantity of acid derivative of saccharide, i.e. 400 g+400 g=800 g (dry) used within such a mixture.

This example confirms that it is possible to obtain an oxidation reaction with undreamed-of selectivity and yield by using extremely low quantities of catalyst(s) (molybdenum and/or tungsten), especially with respect to those advocated in the EVERETT document quoted before.

In the present case, the substrate is made up in total of 2×(2.24+0.046) or 4.572 moles of acid derivative of saccharide (GDL) and of salt of acid derivative of saccharide (sodium gluconate). The oxidation is carried out in the presence of 0.017 mole molybdenum as indicated above and thus of 0.017/4.572 or 0.0037 equivalent of molybdenum approximately. In weight, this concentration corresponds to 1.62 g molybdenum for 820 g substrate (GDL+sodium gluconate), or approximately 0.2% molybdenum in relation to the total weight of acid derivative of saccharide and of salt of acid derivative of saccharide.

For its part, the copper sulfate pentahydrate is here introduced at a concentration of 0.4 g for 820 g substrate or approximately 0.05% and thus roughly 4 times weaker again than the concentration in weight of molybdenum (0.2%).

This example confirms the interest in associating the catalysts used according to the invention, i.e. tungsten and molybdenum, with doping agents such as copper salts.

What is claimed is:

1. A method of manufacturing an aldose or an aldose derivative containing n carbon atoms on the hydrocarbonic chain, wherein in an aqueous phase at least one starting material selected from an acid derivative of saccharide with n+1 carbon atoms containing at least one α-hydroxy acid unit, or a salt of such an acid derivative of saccharide is brought into contact with hydrogen peroxide in the presence of a quantity of at least one tungsten or molybdenum salt, said quantity being less than 4 equivalents, expressed as the total number of moles of tungsten and molybdenum divided by the total number of moles of acid derivative(s) of saccharide and of salt(s) of acid derivative(s) of saccharide.

2. The manufacturing method of claim 1, wherein the quantity of at least one tungsten or molybdenum salt is less than 2 equivalents.

3. The manufacturing method according to claim 1, wherein any acid derivative of saccharide and/or any salt of acid derivative of saccharide is provided, in liquid and/or solid form, in such a quantity that the total concentration of acid derivative(s) of saccharide and salt(s) of acid derivative (s) of saccharide, in the reaction medium, is between 1 and 90%, expressed in dry weight in relation to the total, weight of the reaction medium.

4. The manufacturing method according to claim 3, wherein any acid derivative of saccharide and/or any salt of acid derivative of saccharide is provided, in liquid and/or solid form, in such a quantity that the total concentration of acid derivative(s) of saccharide and salt(s) of acid derivative (s) of saccharide, in the reaction medium, is between 20 and 90%.

5. The manufacturing method according to claim 2, wherein the quantity of tungsten and molybdenum salt(s) is less than 1 equivalent, expressed in the total number of moles of tungsten and molybdenum divided by the total number of moles of acid derivative(s) of saccharide and of salt(s) of acid derivative(s) of saccharide.

6. The manufacturing method according to claim 5, wherein the quantity of tungsten and molybdenum salt(s) is between 0.001 and 50%, expressed in weight of tungsten and of molybdenum in relation to the dry weight of acid derivative(s) of saccharide and of salt(s) of acid derivative(s) of saccharide used.

7. The manufacturing method according to claim 6, wherein the quantity of tungsten and molybdenum salt(s)is between 0.001 and 20%.

8. The manufacturing method according to claim 7, wherein the quantity of tungsten and molybdenum salt(s) is between 0.001 and 10%.

9. The manufacturing method according to claim 1, wherein as substrate brought into contact with the hydrogen peroxide, a mixture is used containing at least one acid derivative of saccharide, in free and/or lactonised form, and at least one salt of an acid derivative of saccharide.

10. The manufacturing method according to claim 9, wherein the at least one salt of an acid derivative of saccharide is an alkaline or alkaline earth salt.

11. The manufacturing method according to claim 9, wherein the dry weight of salt(s) of acid derivative(s) of saccharide within the mixture represents between 0.5 and 20%, of the dry weight of acid derivative(s) of saccharide contained in said mixture.

12. The manufacturing method according to claim 11, wherein the dry weight of salt(s) of acid derivative(s) of saccharide within the mixture represents between 1 and 10%, of the dry weight of acid derivative(s) of saccharide contained in said mixture.

13. The manufacturing method according to claim 1, wherein the acid derivative of saccharide is an aldonic acid, in free and/or lactonised form, and that the salt of acid derivative of saccharide is a salt of aldonic acid.

14. The manufacturing method according to claim 13, wherein the acid derivative of saccharide is a gluconic acid, in free and/or lactonised form.

15. The manufacturing method according to claim 13, wherein the salt of acid derivative of saccharide is a salt of gluconic acid.

16. The manufacturing method according to claim 15, wherein the salt of gluconic acid is an alkaline or alkaline earth salt of gluconic acid.

17. The manufacturing method according to claim 1, wherein the tungsten or molybdenum salt is chosen from the group comprising oxides, acids, heteropolyacids, alkaline metal salts, alkaline earth metal salts and ammonium salts.

18. The manufacturing method according to claim 17, wherein the tungsten or molybdenum salt is chosen from the group comprising the alkaline salts, alkaline earth salts and ammonium salts of tungsten and of molybdenum.

19. The manufacturing method according to claim 1, which is carried out in the presence of at least one doping agent chosen from metallic salts, based on metals other than tungsten and molybdenum.

20. The manufacturing method according to claim 19, wherein the at least one doping agent is chosen from copper salts.

21. The manufacturing method according to claim 19, which is carried out in the presence of between 0.0001 and 1% doping agent(s), this concentration being expressed in total dry weight of doping agent(s) in relation to the total dry weight of acid derivative(s) of saccharide and of salt(s) of acid derivative(s) of saccharide present in the reaction medium.

22. The manufacturing method according to claim 21, which is carried out in the presence of between 0.001 and 0.5%, doping agent(s).

* * * * *

UNITED STATES PATENT AND TRADEMARK OFFICE
CERTIFICATE OF CORRECTION

PATENT NO. : 6,476,217 B1
DATED : November 5, 2002
INVENTOR(S) : Rodolphe Tamion It is certified that error appears in the above-identified patent and that said Letters Patent is hereby corrected as shown below:

<u>Title page,</u>
Item [22] Filed, the filing date should be -- December 2, 1999 --.

Signed and Sealed this

Fifteenth Day of April, 2003

JAMES E. ROGAN
*Director of the United States Patent and Trademark Office*